US010010453B2

(12) United States Patent
Harima et al.

(10) Patent No.: US 10,010,453 B2
(45) Date of Patent: Jul. 3, 2018

(54) ADHESIVE PATCH (75) Inventors: Jun Harima, Ibaraki (JP); Masakatsu Konno, Ibaraki (JP); Ryo Hashino, Ibaraki (JP); Akira Numata, Ibaraki (JP)

(73) Assignee: NITTO DENKO CORPORATION, Osaka (JP)

( * ) Notice: Subject to any disclaimer, the term of this patent is extended or adjusted under 35 U.S.C. 154(b) by 118 days.

(21) Appl. No.: 12/548,571

(22) Filed: Aug. 27, 2009

(65) Prior Publication Data

US 2010/0056972 A1 Mar. 4, 2010

(30) Foreign Application Priority Data

Aug. 28, 2008 (JP) .................................. 2008/219189

(51) Int. Cl.
*A61F 13/00* (2006.01)
*A61F 13/02* (2006.01)

(52) U.S. Cl.
CPC ...... *A61F 13/0203* (2013.01); *A61F 13/0276* (2013.01); *A61F 2013/00587* (2013.01)

(58) Field of Classification Search
USPC ............. 602/41–49; 128/888, 889; D24/189; 604/304–308
See application file for complete search history.

(56) References Cited

U.S. PATENT DOCUMENTS

| | | | |
|---|---|---|---|
| 5,520,762 A * | 5/1996 | Rasmussen | A61F 13/023 156/216 |
| 5,591,447 A | 1/1997 | Jensen | |
| 5,944,683 A * | 8/1999 | Baranowski | 602/65 |
| 6,420,623 B2 * | 7/2002 | Augustine et al. | 602/41 |
| 2004/0126413 A1 | 7/2004 | Sigurjonsson et al. | |
| 2005/0147654 A1 | 7/2005 | Matloub et al. | |
| 2005/0214352 A1 * | 9/2005 | Hori | A61K 31/137 424/449 |

(Continued)

FOREIGN PATENT DOCUMENTS

| | | |
|---|---|---|
| EP | 1 944 001 | 7/2008 |
| JP | 06-000201 | 1/1994 |

(Continued)

OTHER PUBLICATIONS

Yao et al; "Embossing-Based Process Variants for Polymer Microfabrication"; Jun. 1, 2005.*

(Continued)

*Primary Examiner* — Ophelia A Hawthorne
*Assistant Examiner* — Caitlin Carreiro
(74) *Attorney, Agent, or Firm* — Wenderoth, Lind & Ponack, L.L.P.

(57) ABSTRACT

An adhesive patch containing an adhesive patch main part containing a support and an adhesive layer laminated on the support, wherein the adhesive patch main part has a peripheral part, a central part, and an intermediate part between the peripheral part and the central part, the intermediate part of the adhesive patch main part has a thickness greater than that of the central part of the adhesive patch main part, and the central part of the adhesive patch main part has a thickness greater than that of the peripheral part of the adhesive patch main part, and a production method thereof.

7 Claims, 5 Drawing Sheets

(56) References Cited

U.S. PATENT DOCUMENTS

| | | | |
|---|---|---|---|
| 2006/0234581 A1* | 10/2006 | Saito | A61K 9/7061 442/149 |
| 2007/0026055 A1 | 2/2007 | Ninomiya et al. | |
| 2007/0068536 A1* | 3/2007 | Rawski | 128/888 |
| 2007/0106195 A1 | 5/2007 | Marcoux et al. | |
| 2008/0108927 A1* | 5/2008 | Sinyagin | A61F 13/00987 602/54 |
| 2010/0215721 A1* | 8/2010 | Noguchi | A61K 9/7061 424/443 |

FOREIGN PATENT DOCUMENTS

| | | | |
|---|---|---|---|
| JP | 6-63071 | | 3/1994 |
| JP | 09-110679 | | 4/1997 |
| JP | 9-124462 | | 5/1997 |
| JP | 2000-37413 | | 2/2000 |
| JP | 2000-037413 A | * | 2/2000 |
| JP | 2000037413 A | * | 2/2000 |
| JP | 2003-526463 | | 9/2003 |
| JP | 2007-063260 | | 3/2007 |
| JP | 2007132218 A | * | 5/2007 |
| NZ | 535694 | | 1/1997 |
| WO | 01/68021 | | 9/2001 |
| WO | 2008/142896 | | 11/2008 |

OTHER PUBLICATIONS

Pure & Appl. Chem., vol. 63, No. 12, pp. 1793-1804,1991.*
JP2000-037413A_translation.pdf.*
"What is pvc.PDF"; Sevenster, Arjen: "What is PVC?"; accessed from www.pvc.org on Oct. 15, 2015.*
Sevenster, Arjen; "What is PVC?"*
Sevenster, Arjen; "What is PVC?"*
Extended European Search Report dated Jul. 12, 2012 in corresponding European Application No. 09 16 8751.
Japanese Office Action dated Nov. 12, 2012 in corresponding Japanese Application No. 2008-219189.
Indian Office Action dated May 8, 2017 in corresponding Indian Patent Application No. 2026/CHE/2009.
Korean Office Action dated Feb. 25, 2016 in corresponding Korean Patent Application No. 10-2009-0080420 with English translation.
Examination Report dated Aug. 28, 2009 in the corresponding New Zealand Patent Application No. 579246.
Japanese Office Action dated Jun. 10, 2014 in corresponding Japanese Patent Application No. 119261/2013 with English translation.

* cited by examiner

FIG. 5 section B-B' (detail)

FIG. 6

ADHESIVE PATCH

This application claims priority to patent application No. 2008-219189 filed in Japan, the contents of which are incorporated in full herein by this reference.

BACKGROUND OF THE INVENTION

I. Technical Field of the Invention

The present invention relates to an adhesive patch comprising a support and an adhesive layer formed on the support, and a production method thereof.

II. Description of the Related Art

In recent years, various adhesive patches and adhesive preparations have been developed. Adhesive patch and adhesive preparation are highly superior from the aspects of wound protection and/or continuous transdermal administration of a drug.

In general, an adhesive patch comprises a support made of a cloth, a plastic film and the like and an adhesive layer laminated on the support, and is generally provided with a release liner laminated on the adhesive layer and in a package made of a resin film and the like.

In such an adhesive patch, when the adhesive layer becomes thick, the edge of the adhesive patch is easily rubbed against clothes and the like and turned up, as well as the components of the adhesive layer protrude from the edge of the adhesive patch, i.e., cold flow, thus posing problems during adhesion to the skin.

Cold flow occurs depending on the property of an adhesive. It often occurs when, in particular, an adhesive patch is under a load for a long time, namely, when an adhesive patch is contained in a package and stored for a long period and the like.

Adverse influences of cold flow include, for example, degraded performance of taking out of an adhesive patch from a package, which is caused by adhesion of protruded adhesive layer components to the inside of the package, edge lifting and staining of the adhesive patch during adhesion to the skin, lower effect of adhesive patch having a medicinal effect and the like. Therefore, an adhesive patch desirably has an edge which is not easily rubbed against clothes and does not permit easy cold flow, and has an adhesive layer retaining the original shape.

To solve these problems, JP-A-2000-37413 discloses an adhesive skin patch which prevents protrusion of a skin adhesive layer from the edge of the adhesive skin patch and edge lifting of the adhesive skin patch by setting the thickness of the skin adhesive layer located at the center of a support film to 0.2-0.5 mm, and the thickness of the peripheral part of the skin adhesive layer to as small as 0.05-0.2 mm by stamping the peripheral part, and a production method thereof.

More particularly, the production method of the adhesive skin patch described in JP-A-2000-37413 is characterized by forming a skin adhesive layer on a release sheet, laminating a support film thereon and punching the resulting laminate sheet in two steps, and includes, after the first punching step, stamping, without heating, to form a peripheral part having a small thickness. To be specific, when the sheet is first stamped and thereafter punched out into a final shape in one step, a skin adhesive layer present between a support film and a release sheet does not move to both sides easily upon stamping, and even if it could, it has no way out. Hence, the skin adhesive layer adjacent to the peripheral part becomes swollen by stamping. The method described in JP-A-2000-37413 intends to avoid formation of such swelling and is characterized in that the sheet is punched out in a larger size and stamped, a skin adhesive layer adjacent to the peripheral part is pushed out from an end surface after the punching processing, and the sheet is punched out into a final shape by the second stage punching processing.

SUMMARY OF THE INVENTION

In the adhesive skin patch described in JP-A-2000-37413, however, the frequency of contact of the edge of the adhesive skin patch with an inner surface of a package is not sufficiently reduced during storage thereof in the package and, when a skin adhesive layer protrudes from the edge of the adhesive skin patch in the package, adhesion of the adhesive skin patch to an inner surface of the package cannot be sufficiently suppressed. As a result, taking the adhesive skin patch out from the inside of the package may become difficult. When the adhesive skin patch could come into contact with clothes and the like during adhesion to the skin, moreover, the frequency of rubbing of the edge of the adhesive skin patch against clothes etc. is not sufficiently reduced and the edge may be turned up. In addition, since the thickness of the skin adhesive layer is smaller in the peripheral part, the skin adhesion may decrease in the peripheral part than in the central part.

The present invention has been made in view of such a situation and aims to provide an adhesive patch, which can be taken out easily from the package, has an edge not turned up easily, shows sufficient skin adhesion, and is highly resistant to detachment from the skin surface, wherein the frequency of contact of the edge of an adhesive patch with an inner surface of a package during preservation in the package can be reduced, even when adhesive layer components protrude in the package from the edge of an adhesive patch, adhesion of the adhesive patch to an inner surface of the package can be suppressed, and the frequency of rubbing of the edge against clothes etc. during adhesion to the skin is reduced, and a production method thereof.

The present inventors have conducted intensive studies and found that the aforementioned problems can be achieved by utilizing formation of swelling by stamping rather than avoiding the swelling, which resulted in the completion of the present invention. Accordingly, the present invention provides the following.

[1] An adhesive patch comprising an adhesive patch main part comprising a support and an adhesive layer laminated on the support, wherein the adhesive patch main part comprises a peripheral part, a central part, and an intermediate part between the peripheral part and the central part, the intermediate part of the adhesive patch main part has a thickness greater than that of the central part of the adhesive patch main part, and the central part of the adhesive patch main part has a thickness greater than that of the peripheral part of the adhesive patch main part.

[2] The adhesive patch of the aforementioned [1], wherein a difference between the highest thickness of the adhesive patch main part in the intermediate part and the thickness of the adhesive patch main part in the peripheral part is 30-3000 μm, a difference between the highest thickness of the adhesive patch main part in the intermediate part and the thickness of the adhesive patch main part in the central part is 15-1500 μm, and a difference between the thickness of the adhesive patch main part in the central part and the thickness of the adhesive patch main part in the peripheral part is 20-2000 µm.

[3] The adhesive patch of the aforementioned [2], wherein the support comprises a resin film having a thickness of 1-45 µm.

[4] The adhesive patch of the aforementioned [1], wherein the support comprises a thermoplastic resin.

[5] The adhesive patch of the aforementioned [4], wherein the thermoplastic resin comprises poly(ethylene terephthalate).

[6] The adhesive patch of the aforementioned [1], wherein the adhesive layer is not cross-linked.

[7] The adhesive patch of the aforementioned [1], wherein the adhesive layer comprises an organic liquid component.

[8] The adhesive patch of the aforementioned [1], comprising a release liner laminated on the adhesive layer.

[9] The adhesive patch of the aforementioned [1], wherein the adhesive layer comprises a drug.

[10] The adhesive patch of the aforementioned [8], wherein the release liner has an extended part outwardly extending beyond the adhesive patch main part.

[11] A method of producing the adhesive patch of the aforementioned [8], comprising heating and pressing an area corresponding to a peripheral part of the adhesive patch main part on the surface on the support side of an adhesive patch original sheet comprising a support, an adhesive layer laminated on the support, and the release liner laminated on the adhesive layer to form an intermediate part having a swollen shape at an inner side of the aforementioned peripheral part.

The adhesive patch of the present invention comprises an adhesive patch main part having a peripheral part and a central part, and further, an intermediate part between the peripheral part and the central part, wherein the intermediate part in the adhesive patch main part has a thickness greater than that of the central part of the adhesive patch main part, and the central part of the adhesive patch main part has a thickness greater than that of the peripheral part of the adhesive patch main part. When the adhesive patch of the present invention is contained in a package, therefore, the intermediate part in the adhesive patch main part fulfills the function based on the swollen shape, and further, the central part fulfills the function to hold up the package. Consequently, the frequency of contact of the edge of an adhesive patch with an inner surface of the package decreases and, even when adhesive layer components protrude or outflow from the edge, adhesion of the adhesive patch to the package can be suppressed. Therefore, the present invention facilitates taking out of an adhesive patch from the package.

When the adhesive patch of the present invention may come into contact with clothes and the like after adhesion to the skin, the frequency of rubbing of the edge of an adhesive patch against clothes and the like can be reduced since the peripheral part of the adhesive patch main part has a small thickness and the intermediate part fulfills the function based on the swollen shape. In addition, since the central part of the adhesive patch main part has a thickness greater than that of the peripheral part of the adhesive patch main part and the central part functions to hold up clothes and the like, the frequency of rubbing of the edge of an adhesive patch against clothes and the like can be further reduced. Moreover, skin adhesion of the adhesive layer of the intermediate part in the adhesive patch main part having a large thickness compensates for the skin adhesion of the adhesive layer of the peripheral part of the adhesive patch main part having a small thickness, whereby the adhesive patch can show sufficient skin adhesion. Furthermore, since the central part of the adhesive patch main part has a thickness smaller than that of the intermediate part in the adhesive patch main part, the intermediate part holds up clothes, whereby the frequency of rubbing of the central part against clothes can be reduced. Therefore, the adhesive patch of the present invention is highly resistant to detachment from the skin surface.

Moreover, in the embodiment of the adhesive patch of the present invention wherein a release liner has an extended part outwardly extending beyond the adhesive patch main part, since the frequency of contact of the edge of the adhesive patch main part against an inner surface of the package is decreased by the extended part during the period when the adhesive patch is contained in the package, even when an adhesive layer component is protruded or outflown from the edge of the adhesive patch main part, adhesion thereof to an inner surface of the package, which prevents easy taking out of the adhesive patch from the package, can be suppressed.

According to the production method of the adhesive patch of the present invention, an adhesive patch which can be easily taken out from a package and is highly resistant to the detachment from the skin surface can be efficiently produced.

DETAILED DESCRIPTION OF THE INVENTION

In the present specification, the "adhesive patch" is a concept embracing not only those free of a drug but also "adhesive preparation" containing a drug. Those containing a drug are sometimes particularly referred to as an "adhesive preparation".

The present invention is explained in detail in the following by referring to the attached drawings. In the drawings, the dimensional size ratios of elements used to explicitly indicate each element are different from actual ratios.

Figure 1:
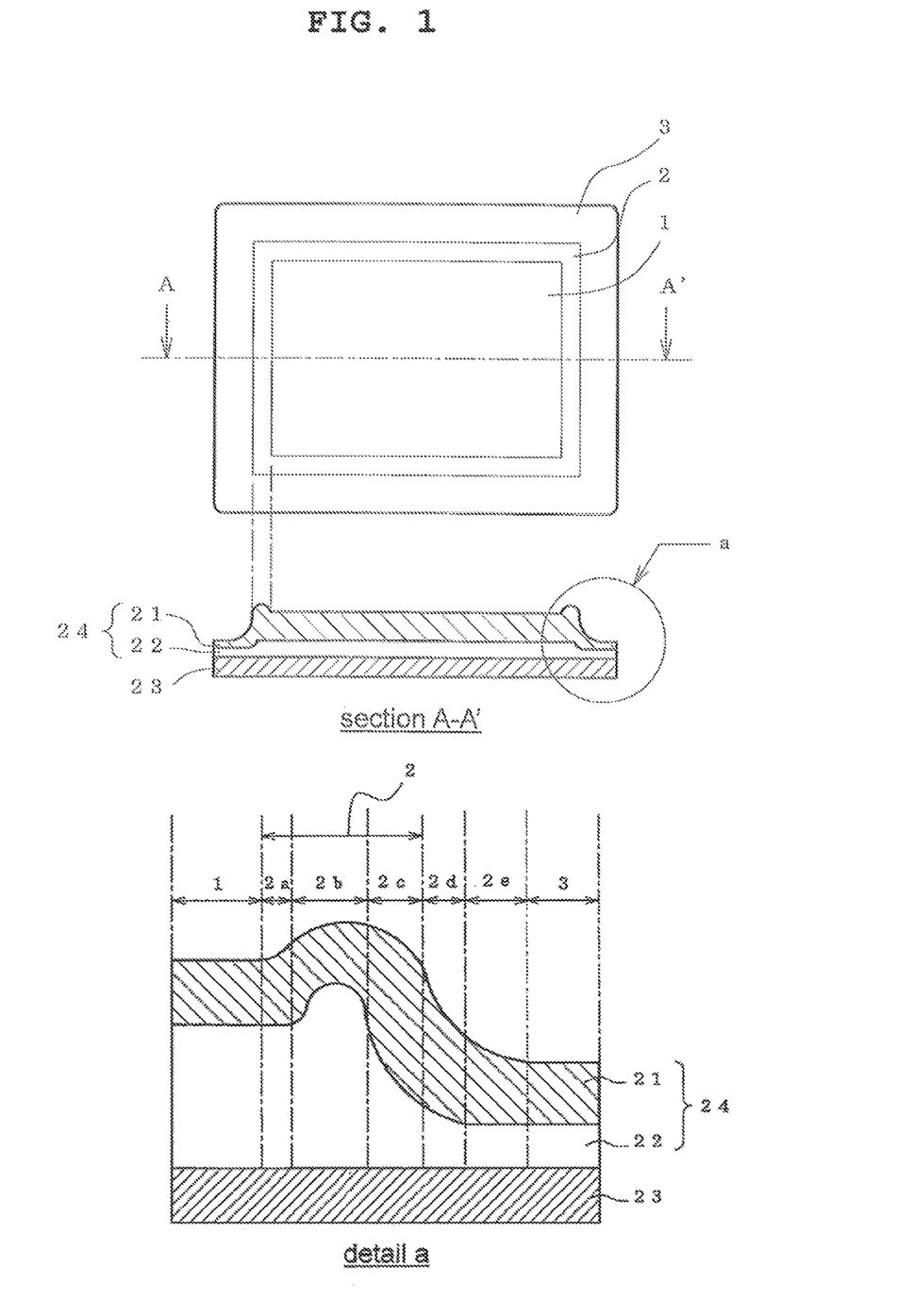
FIG. 1 shows a schematic plane view, a schematic sectional view and the detail thereof, which show the shape of one embodiment of the adhesive patch of the present invention.

FIG. 1 shows schematic diagrams of one embodiment of the adhesive patch of the present invention. The adhesive patch of the present invention comprises an adhesive patch main part 24 comprising a support 21 and an adhesive layer 22 formed on the support 21, and may have a release liner 23 which is laminated on the adhesive surface (to be in contact with the skin) of the adhesive layer 22 of the adhesive patch main part 24, and protects the adhesive surface until adhered to the skin. In the adhesive patch of the present invention, the adhesive patch main part 24 has a peripheral part 3, and a central part 1, and further has an intermediate part 2 between the peripheral part 3 and the central part 1, wherein the thickness of the intermediate part 2 of the adhesive patch main part 24 is greater than that of the central part 1 of the adhesive patch main part 24, and the thickness of the central part 1 of the adhesive patch main part 24 is greater than that of the peripheral part 3 of the adhesive patch main part 24.

As shown in the detail a in FIG. 1, the surface of the support is almost flat for the central part 1 and the peripheral part 3, and examples of the area where the support has a curved surface include
1) region 2a where an adhesive layer 22 has the same thickness as that of the central part 1 but the height of the surface of a support 21 becomes increasingly greater than that of the central part 1 in the direction from the central part 1 toward a region 2b;
2) region 2b where the thickness of the adhesive layer 22 is greater than that of the central part 1, and the height of the surface of the support 21 is greater than that of the central part 1;
3) region 2c where the thickness of the adhesive layer 22 becomes increasingly smaller than that of the central part 1 in the direction from the central part 1 toward a region 2d and is greater than that of the peripheral part 3, but the height of the surface of the support 21 is greater than that of the central part 1;
4) region 2d where the thickness of the adhesive layer 22 is smaller than that of the central part 1 and greater than that of the peripheral part 3, but the height of the surface of the support 21 becomes increasingly smaller than that of the central part 1 in the direction from the central part 1 toward a region 2e and is greater than that of the peripheral part 3; and
5) region 2e where the thickness of the adhesive layer 22 is the same as that of the peripheral part 3 but the height of the surface of the support 21 is greater than that of the peripheral part 3.

The intermediate part 2 in the present invention refers to an area where the height of the surface of the support 21 is greater than that of the central part 1, namely, an area shown by region 2 comprising regions 2a, 2b and 2c in FIG. 1. Therefore, the intermediate part 2 includes an area where the thickness of the adhesive layer 22 is the same as that of the central part 1, an area where the thickness is greater than that of the central part 1, and an area where the thickness is smaller than that of the central part 1.

The adhesive patch of the present invention has a substantially flat plane form. The flat shape of the adhesive patch of the present invention includes, but is not limited to, for example, a rectangle as shown in FIG. 1, polygon such as triangle, pentagon and the like, or a shape defined by straight lines, a shape defined by curved lines such as ellipse, circular shape and the like and a combination thereof. The size of the adhesive patch is not limited, and can be selected to be appropriate according to the use, size of application site and the like. For example, when the adhesive patch has a rectangular shape as shown in FIG. 1, the length of one side thereof is generally 30-90 mm, and the length of other side orthogonal to said side is generally 30-90 mm.

Figure 2:
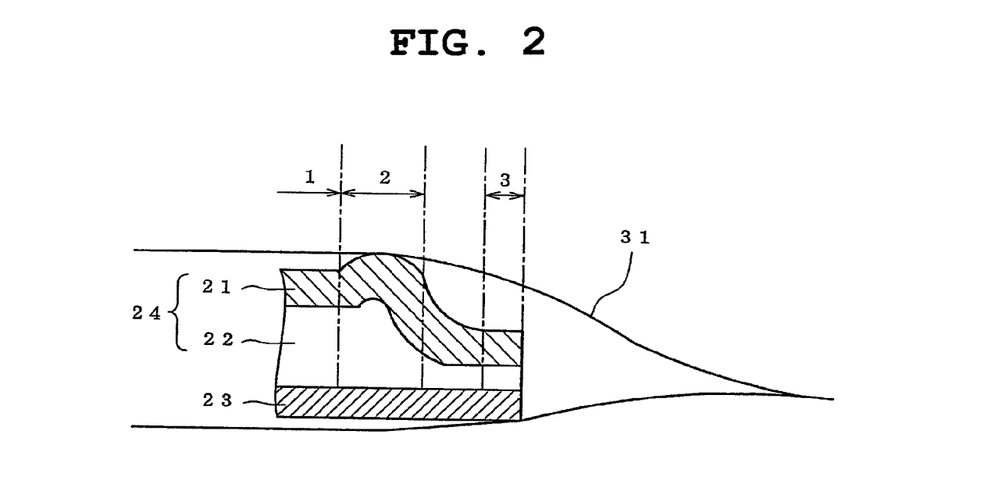
FIG. 2 is a schematic sectional view showing an embodiment of the adhesive patch of the present invention contained in a package, which limitatively shows the characteristic shape mainly of the intermediate part.

FIG. 2 is a schematic view showing an embodiment of the adhesive patch of the present invention contained in a package, which limitatively shows the characteristic shape mainly of the intermediate part. As shown in FIG. 2, when the adhesive patch is contained in a package 31, the intermediate part 2 in the adhesive patch main part fulfills the function based on a swollen shape, and the frequency of contact of the edge of the adhesive patch to the inside of the package 31 decreases. That is, the thickness of the adhesive patch main part 24 varies between the intermediate part 2 and the peripheral part 3, and the thickness of the intermediate part 2 is greater than that of the peripheral part 3. Such difference in the thickness affords the function of the intermediate part 2 to hold up the package 31. As a result, the frequency of contact of the edge of the adhesive layer 22 against an inner surface of the package decreases. Therefore, during storage of an adhesive patch in a sealed package, adhesion of the adhesive patch to an inner surface of the package due to protrusion of the adhesive layer components such as additive and the like from the edge of the adhesive patch can be effectively suppressed. Hence, the adhesive patch of the present invention enables easy removal of the adhesive patch from the package.

In addition, the thickness of the adhesive patch main part 24 is greater in the central part 1 than in the peripheral part 3. Such difference in the thickness affords the function of the central part 1 to hold up the package 31. As a result, the frequency of contact of the edge of the adhesive layer 22 against an inner surface of the package further decreases and adhesion of the adhesive patch to an inner surface of the package can be effectively suppressed.

Figure 3:
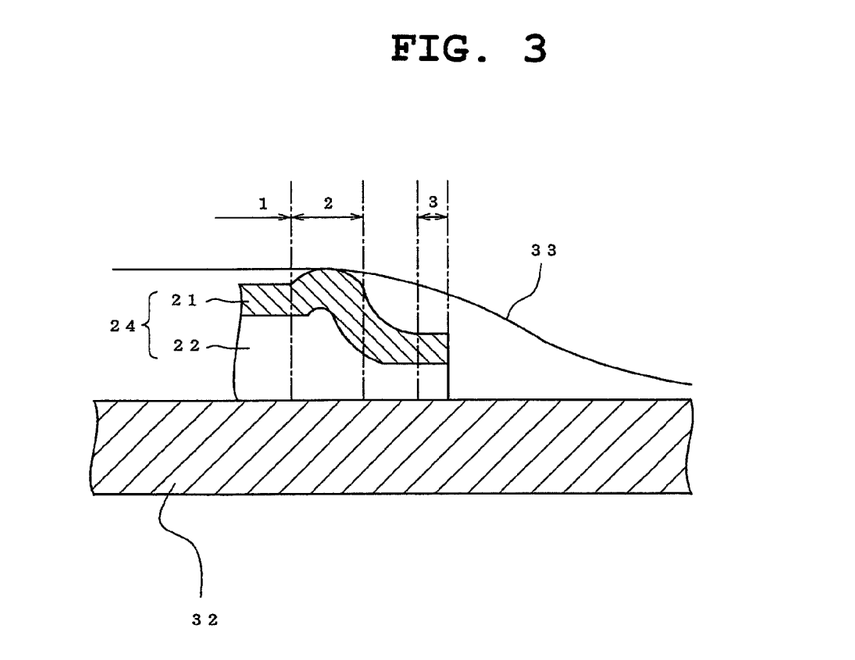
FIG. 3 is a schematic sectional view showing an embodiment of the adhesive patch of the present invention, which is adhered to the skin and in contact with clothes, limitatively based on the characteristic shape mainly of the intermediate part.

FIG. 3 is a schematic view showing an embodiment of the adhesive patch of the present invention, which is adhered to the skin and in contact with clothes, limitatively based on the characteristic shape mainly of the intermediate part. As shown in FIG. 3, the intermediate part 2 fulfills the function based on a swollen shape. As a result, when the adhesive patch of the present invention is adhered to a skin 32, the frequency of rubbing of the edge of the adhesive patch against clothes 33 that can be in contact with the adhesive patch can be reduced. That is, the thickness of the adhesive patch main part 24 is greater in the intermediate part 2 than in the peripheral part 3. Such difference in the thickness affords the function of the intermediate part 2 to hold up the clothes 33. As a result, the frequency of rubbing of the edge of the adhesive layer 22 against the clothes 33 can be reduced.

In addition, when the adhesive patch of the present invention is adhered to the skin 32, since the thickness of the adhesive patch main part 24 is greater in the central part 1 than in the peripheral part 3, such central part 1 can fulfill the function to hold up the clothes 33. As a result, the frequency of rubbing of the edge of the adhesive patch against the clothes 33 can be further reduced. Moreover, since the thickness of the central part 1 of the adhesive patch main part 24 is smaller than that of the intermediate part 2 of the adhesive patch main part 24, the intermediate part 2 holds up the clothes 33, and the frequency of rubbing of the central part 1 against the clothes 33 can be reduced. Hence, the adhesive patch of the present invention does not easily fall from the skin.

Furthermore, the adhesive layer 22 in the intermediate part 2 having a thickness greater than that of the adhesive layer 22 of the central part 1 (e.g., the adhesive layer in the region 2b in FIG. 1) affords greater skin adhesion than that of the adhesive layer 22 of the central part 1, and compensates for skin adhesion of the adhesive layer 22 of the peripheral part 3 of the adhesive patch main part having a smaller thickness, thus providing a sufficient skin adhesion to the adhesive patch. Hence, the adhesive patch of the present invention is highly resistant to detachment from the skin surface.

Now the shape and size of the adhesive patch main part of the present invention, particularly a characteristic shape thereof, will be more specifically explained. The shape of the flat plane of the peripheral part preferably has a band-like part having a width of 0.29-5 mm, more preferably 0.29-3.5 mm. By setting the width of the peripheral part to fall within the above-mentioned range, protrusion or outflow of an adhesive layer component from the edge of the adhesive patch can be more effectively suppressed, and the peripheral part of the adhesive layer does not become too large. Thus, a decrease in the adhesiveness of the peripheral part of the adhesive patch can be prevented more effectively. To sufficiently achieve the effect of the present invention, the adhesive patch preferably has such a band-like part in each peripheral part.

The thickness of the adhesive layer in the central part is, for example, 50-5000 μm, preferably 150-4000 μm. By employing the above-mentioned range, a decrease in the adhesiveness can be prevented more effectively, and the shape of the adhesive layer can be easily maintained. Therefore, protrusion of an adhesive layer component from the edge of the adhesive patch can be suppressed more effectively.

The thickness of the adhesive layer in the peripheral part is preferably not less than 1.5 μm so as to ensure the necessary skin adhesiveness, and preferably not more than 50 μm so as to more effectively suppress protrusion or outflow of an adhesive layer component from the edge of the adhesive patch. The difference in the thickness of the adhesive patch main part in the central part and the thickness of the adhesive patch main part in the peripheral part is preferably 20-2000 μm so as to hold up a package or clothes in the central part, reduce the frequency of rubbing of the edge of the adhesive patch main part against a package or clothes, and impart necessary adhesiveness to the adhesive layer in the central part.

Since the thickness of the support is almost constant from the peripheral part to the central part, the difference in the thickness of the adhesive layer in the central part and the thickness of the adhesive layer in the peripheral part is the same as mentioned above.

To exert the function based on the swollen shape as mentioned above, the difference in the highest thickness of the adhesive patch main part in the intermediate part and the thickness of the adhesive patch main part in the peripheral part is preferably 30-3000 μm, more preferably 50-1000 μm. Since the thickness of the support is almost constant from the peripheral part to the central part, the difference in the highest thickness of the adhesive layer in the intermediate part and the thickness of the adhesive layer in the peripheral part is the same as mentioned above. When these differences are set to 30-3000 μm, the aforementioned effect of compensating the skin adhesiveness can be sufficiently obtained. When the upper limit of the aforementioned difference is 3000 μm, flexibility of the adhesive patch is achieved and the adhesive patch is compact and easily handled.

To hold up clothes by the intermediate part, and reduce the frequency of rubbing of the central part against clothes, the difference between the highest thickness of the adhesive patch main part in the intermediate part and the thickness of the adhesive patch main part in the central part is preferably 15-1500 μm. Since the thickness of the support is almost constant from the peripheral part to the central part, the difference in the highest thickness of the adhesive layer in the intermediate part and the thickness of the adhesive layer in the central part is the same as mentioned above. In addition, to exert the function based on the swollen shape, the width of the intermediate part is preferably 100-10000 μm.

While the support of the above-mentioned adhesive patch is not particularly limited, a support which is substantially drug impermeable, namely, a support which does not permit an active ingredient, an additive and the like in the adhesive layer to pass through the support and be lost from the adhesive patch to cause a decreased content is preferable.

In the present invention, the support is preferably a laminate of a porous material and a resin film, wherein an adhesive layer is laminated on the porous material of the laminate. A porous material has concaves and convexes on the surface and such unevenness is considered to suppress movement or disappearance of voids (air bubbles) possibly contained in the adhesive layer. Therefore, using the porous material, outflow and protrusion of adhesive layer components can be suppressed. When a porous material is used, since it contains voids (air bubbles), it is considered that the voids move to the adhesive layer of the peripheral part of the adhesive patch, and are fused with air bubbles in the adhesive layer to possibly form greater air bubbles in the peripheral part, whereby the effect of the present invention is enhanced. Since adhesive layer components that outflow from the edge of the adhesive patch can enter the space in air bubbles, the air bubbles can effectively suppress outflow and protrusion of the adhesive layer components.

Examples of the porous material include porous film and sheet. When the sheet has a thickness of not less than 200 μm, a porous film is preferable. The aforementioned porous film may be a single layer film or a laminate film, and one having an anchoring ability to suppress movement of the adhesive layer to the porous material can be preferably used. Specific examples include paper, woven fabric, non-woven fabric, knitted fabric, mechanically perforated-treated film and metal foil, laminates thereof and the like. Of these, paper, woven fabric, non-woven fabric, and laminates thereof are particularly preferable from the aspects of handling, performance and the like, and non-woven fabric is especially preferable.

The resin film may be a single layer film or a laminate film, with preference given to a non-porous film composed of a resin impermeable to active ingredients.

The porous film and resin film may be made of similar materials or different materials. These films can be laminated according to a known method. They may contain various additives such as antioxidant, pigment, antistatic agent and the like when appropriate as long as the effect of the invention and effect of the adhesive patch are not impaired. In addition, the surface thereof may be subjected to a corona discharge treatment, an ultraviolet irradiation treatment and the like.

Examples of the material of such porous film and resin film constituting the support include polyester, nylon, SARAN (registered trade mark of Asahi Kasei Corporation or Dow Chemical Company, USA), polyethylene, polypropylene, poly(vinyl chloride), ethylene-ethyl acrylate copolymer, poly(tetrafluoroethylene), SURLYN (registered trade mark of DuPont, USA), combinations thereof and the like.

Such resin films suppress permeation of adhesive layer components through the support to reduce the content thereof. In addition, when the adhesive layer contains a drug, they are preferably used to achieve an effect of what is called an occlusive dressing technique (ODT).

When the below-mentioned production method of the adhesive patch of the present invention characterized by pressing and heating the area corresponding to the peripheral part of the adhesive patch main part is employed, in order to secure swelling of the intermediate part in the adhesive patch main part, the materials of the porous film and the resin film constituting the support are preferably thermoplastic resins, for example, polyester, polypropylene, polyethylene and the like, and particularly preferably polyester, for example, poly(ethylene terephthalate), since they become soft by heating, are deformed thereafter, and maintain the deformed shape after cooling.

The thickness of the porous film is preferably within the range of 10-100 μm so as to afford improved anchoring ability, flexibility of the entire adhesive patch, adhesion operability and the like. When a woven fabric or non-woven fabric is used as a porous film, the basis weight thereof is preferably 5-50 g/m$^2$, more preferably 10-30 g/m$^2$, to secure air bubbles having an effective size and achieve anchoring.

In the present invention, the thickness of the porous film is measured by staining an adhesive patch with an aqueous ruthenium acid solution, imaging a section produced with a freezing microtome with an FE-SEM (Hitachi, S-4800) at 50- to 1000-power, and reading the gauge scale. In this case, concaves and convexes are present on the surface of the porous film. In a sectional image, 10 convexes are selected at random, and an average of the thickness of the porous film at the convexes is calculated and taken as the thickness of the porous film.

In the present invention, the basis weight of the porous film is determined by multiplying the thickness of the above-mentioned porous film by the specific gravity (apparent specific gravity) of the porous film and calculating the weight of the porous film per unit area.

While the thickness of the resin film is not particularly limited, it is preferably 1-45 μm. When it is not less than 1 μm, a shape wherein the intermediate part in the adhesive patch main part is thicker than the peripheral part of the adhesive patch main part and the central part of the adhesive patch main part can be easily maintained. When it is not more than 45 μm, the rigidity of the resin film cannot possibly develop an uncomfortable feeling during adhesion to the skin. Moreover, when the below-mentioned production method characterized by pressing and heating the area corresponding to the peripheral part of the adhesive patch main part is employed, the swelling of the intermediate part in the adhesive patch main part can be certainly obtained. In the present invention, the thickness of the resin film is measured in the same manner as for the above-mentioned porous film.

Thus, a desirable support in the present invention is a laminate film of a polyester film with 1-45 μm thickness (preferably, poly(ethylene terephthalate) film) and a non-woven fabric made of polyester (preferably, poly(ethylene terephthalate)) having a basis weight of 10-30 g/m$^2$.

In consideration of the skin-following ability and comfortableness during application of an adhesive patch, the total thickness of the support is preferably 5-200 μm.

Now, a production method of a composition for forming an adhesive layer (composition for adhesive layer formation) and the amounts of components constituting the adhesive layer are explained. The amount of each component described in the following for the preparation of the composition for adhesive layer formation is a ratio in wt % of the amount of each component relative to the amount of whole components except solvent (organic solvent).

The adhesive layer can be formed by mixing an adhesive with components such as a drug, a tackifier, an organic liquid component and the like as necessary in the presence of a solvent to give a composition for adhesive layer formation, forming layers thereof by a method such as coating and the like, and drying the layers. The adhesive layer is preferably a hydrophobic adhesive layer in view of adhesion to the skin, and therefore, an anhydrous adhesive layer is preferable. From such aspect, the aforementioned solvent is preferably an organic solvent.

While the organic solvent is not limited, one having compatibility with the aforementioned respective components constituting the adhesive layer and easily volatilizable during a drying process is preferable. Examples of the organic solvent include aromatic hydrocarbons such as toluene, xylene and the like, aliphatic hydrocarbons such as hexane and the like, esters such as ethyl acetate and the like, alcohols such as ethanol and the like, ethers such as diethyl ether, tetrahydrofuran, etc. and the like. These may be used alone or in a mixture of two or more kinds thereof in combination.

The aforementioned drying may be performed by air-drying, or according to a known method using a dryer, hot air, far-infrared radiation and the like.

While the method of mixing the aforementioned respective components is not limited, examples thereof include kneading machines such as a kneader, a planetary mixer and the like, dispersion machines such as homogenizer and the like, stirring machines such as propeller-type blade stirring machine, etc. and the like. These can be used alone or in a combination of two or more kinds thereof.

While the adhesive constituting the adhesive layer is not particularly limited, examples thereof include acrylic-based adhesives comprising acrylic-based polymer; styrene-diene-styrene block copolymers (e.g., styrene-isoprene-styrene block copolymer, styrene-butadiene-styrene block copolymer, etc.); rubber-based adhesives such as polyisoprene, polyisobutylene, polybutadiene and the like; silicone-based adhesives such as silicone rubber, dimethylsiloxane-based, diphenylsiloxane-based and the like; vinyl ether-based adhesives such as poly(vinyl methyl ether), poly(vinyl ethyl ether), poly(vinyl isobutyl ether) and the like; vinyl ester-based adhesives such as vinyl acetate-ethylene copolymer and the like; polyester-based adhesives comprising carboxylic acid component such as dimethyl terephthalate, dimethyl isophthalate, dimethyl phthalate and the like, and polyvalent alcohol components such as ethylene glycol, etc. and the like.

The adhesive layer may be a cross-linked adhesive layer obtained by a cross-linking treatment or a non-cross-linked adhesive layer obtained without a cross-linking treatment. Here, the cross-linking treatment refers to a known treatment applied to an adhesive layer so as to simultaneously achieve sufficient maintenance of skin adhesiveness of the adhesive patch, and suppression of skin irritation to a low level, which is caused by stretching the skin and physically scraping the stratum corneum of the skin to peel off the adhesive patch from the skin surface. Examples of the cross-linking treatment include a chemical crosslinking treatment, a treatment for ion cross-linking, and a physical crosslinking treatment using electron beam, ultraviolet light and the like. Examples of the crosslinking agent include metal salts such as zinc acetate and the like, an epoxy compound, an amide compound, an amine compound, acid anhydride, peroxide, an isocyanate compound and the like.

When the adhesive layer is a non-cross-linked adhesive layer, adhesive layer components tend to protrude or outflow from the edge of the adhesive patch. Even when the adhesive layer is a non-cross-linked adhesive layer, the adhesive patch of the present invention can effectively suppress protrusion and outflow of the adhesive layer components, and is particularly advantageous in such case.

Similarly, when the adhesive layer is an adhesive layer comprising a rubber-based adhesive, adhesive layer components tend to protrude or outflow from the edge of the adhesive patch, and the adhesive patch of the present invention is particularly advantageous in such case.

To achieve appropriate adhesive force and dissolution property of drugs, a rubber-based adhesive is a mixture of the same component or different components having different average molecular weights. To explain with polyisobutylene as an example, a mixture of high molecular weight polyisobutylene having a viscosity average molecular weight of 1,800,000-5,500,000, medium molecular weight polyisobutylene having a viscosity average molecular weight of 40,000-85,000 and, where necessary, lower molecular weight polyisobutylene is preferable. The viscosity average molecular weight in the present invention is determined by calculating a Staudinger index ($J_0$) according to the Schulz-Blaschke equation from the flow time of capillary 1 of Ubbelohde viscometer at 20° C., and from the following formula using the obtained $J_0$ value:

$$J_0 = \eta_{sp} / \{c(1+0.31\eta_{sp})\} \quad \text{(Schulz-Blaschke equation)}$$

$\eta_{sp} = t/t_0 - 1$
t: flow time of solution (by Hagenbach-couette correction equation)
$t_0$: flow time of solvent (by Hagenbach-couette correction equation)
c: concentration of solution (g/cm$^3$)
$J_0 = 3.06 \times 10^{-2} \, Mv^{0.65}$
Mv: viscosity average molecular weight Here, it is preferable to contain high molecular weight polyisobutylene in a proportion of 10-80 wt %, preferably 10-50 wt %, medium molecular weight polyisobutylene in a proportion of 0-90 wt %, preferably 10-80 wt %, and low molecular weight polyisobutylene in a proportion of 0-80 wt %, preferably 0-60 wt %. A generally obtained adhesive layer becomes stiff when the proportion of a high molecular weight component increases, and soft when the proportion of a low molecular weight component increases.

To confer an adequate adhesiveness to the adhesive layer, for example, a tackifier such as rosin-based resin, polyterpene resin, chroman-indene resin, petroleum-based resin, terpene-phenol resin, xylene resin and the like may be added. These may be used alone or in a mixture of two or more kinds thereof. Examples of the aforementioned petroleum-based resin include aliphatic series (C5 series) petroleum resin, aromatic series (C9 series) petroleum resin, copolymer series (C5-C9 series) petroleum resin and alicyclic saturated hydrocarbon resin obtained by partially or completely hydrogenating aromatic series (C9 series) petroleum resin. As the alicyclic saturated hydrocarbon resin, one having a softening point (ring and ball method) of 90-150° C. is preferable. While the amount of the tackifier is not limited, it is, for example, 10-40 wt % so as to impart appropriate adhesiveness and prevent saturation of the effect of a tackifier due to an increased amount thereof.

When desired, the adhesive patch of the present invention can contain a drug in an adhesive layer, whereby an adhesive preparation can be provided. The drug here is not particularly limited, and a transdermally absorbable drug that can be administered to mammals such as human and the like through the skin is preferable.

Specific examples of such drug include general anesthetics, hypnotic sedatives, antiepileptic drugs, antipyretic analgesic antiphlogistic drugs, anti-vertiginous drugs, psychoneurotic drugs, topical anesthetics, skeleton muscle relaxants, autonomic drugs, antispasmodic drugs, anti-parkinsonian drugs, anti-histamine drugs, cardiac stimulants, drugs for arrhythmia, diuretic, hypotensive drug, vasoconstrictor, coronary vasodilator, peripheral vasodilators, arteriosclerosis drugs, drugs for circulatory organ, anapnoics, antitussive expectorant, hormone drugs, external drugs for purulent diseases, analgesic-antipruritic-styptic-antiphlogistic drugs, drugs for parasitic skin diseases, hemostatic drugs, gout treatment drugs, drugs for diabetes, anti-malignant tumor agents, antibiotic, chemical therapy agents, narcotic, quit smoking aids and the like.

While the content of the drug is not particularly limited as long as it can afford an effect by transdermal absorption and does not impair adhesion property of the adhesive, it is preferably 0.1-60 wt %, more preferably 0.1-40 wt %. When the content is not less than 0.1 wt %, a sufficient treatment effect can be obtained. When the content is not more than 60 wt %, the possibility of developing skin irritation is eliminated and economic advantage can also be afforded.

When desired, the adhesive layer can contain an organic liquid component. The organic liquid component is not particularly limited, and examples thereof include glycols such as ethylene glycol, diethylene glycol, propylene glycol, dipropylene glycol, tripropylene glycol, triethylene glycol, poly(ethylene glycol), poly(propylene glycol) and the like; fats and oils such as olive oil, castor oil and the like; lanolin; hydrocarbons such as squalane and liquid paraffin; various surfactants; ethoxylated stearyl alcohol; glycerol monoesters such as oleic acid monoglyceride, caprylic acid monoglyceride and lauryl acid monoglyceride; dialkyl ester of polyalkylene glycol such as poly(propylene glycol); glycerol diester such as glycerol diacetate and the like, glycerol triester such as glycerol triacetate and the like, or a mixture thereof; fatty acid alkyl ester such as triethyl citrate and the like; long chain alcohol; higher fatty acid such as oleic acid and caprylic acid; alkyl ester of higher fatty acid such as isopropyl myristate; pyrrolidones such as N-methylpyrrolidone and N-dodecylpyrrolidone; sulfoxides such as decyl methyl sulfoxide; 1,3-butanediol and the like. These can be used alone or in a mixture of two or more kinds thereof.

The content of the organic liquid component is preferably 10-60 wt, more preferably 15-60 wt %, most preferably 20-60 wt %. When the content of the component is not less than 10 wt %, the adhesive layer is easily plasticized, and adhesive layer components are easily protruded or outflown from the edge of the adhesive layer. Therefore, the present invention capable of effectively suppressing such phenomenon is advantageous in such case. When the content of the organic liquid component is not more than 60 wt %, a given form of the adhesive layer can be easily maintained.

A release liner to protect the adhesive surface can be laminated on the adhesive surface of the adhesive layer of the adhesive patch main part, before applying the adhesive patch main part to the skin. The release liner is not particularly limited, and examples of the material thereof include those known per se in the field. Specific examples thereof include plastic films of polyesters such as poly(ethylene terephthalate), poly(vinyl chloride), poly(vinylidene chloride), various acrylic-based and methacrylic-based polymers, polystyrene, polycarbonate, polyimide, acetyl cellulose, regenerated cellulose (cellophane), celluloid and the like, a laminate film of high-quality paper, glassine paper and the like and polyolefin and the like. For safety, economic efficiency and drug-transfer properties, a polyester film is preferably used.

The release liner is preferably treated for easy peeling on the interfacial surface side with an adhesive, so as to facilitate peeling from the adhesive layer. While the easy peeling treatment is not limited, a known method can be applied. For example, a treatment for forming a peeling-treated layer using a release agent containing a curable silicone resin as a main component by a coating method such as bar coating, gravure coating and the like can be applied.

The thickness of the peeling-treated layer is preferably 0.01-5 μm to ensure release property and uniformity of the coating. The thickness of the release liner having a peeling-treated layer is generally 10-200 μm, preferably 50-100 μm, from the aspect of handling property.

Figure 4:
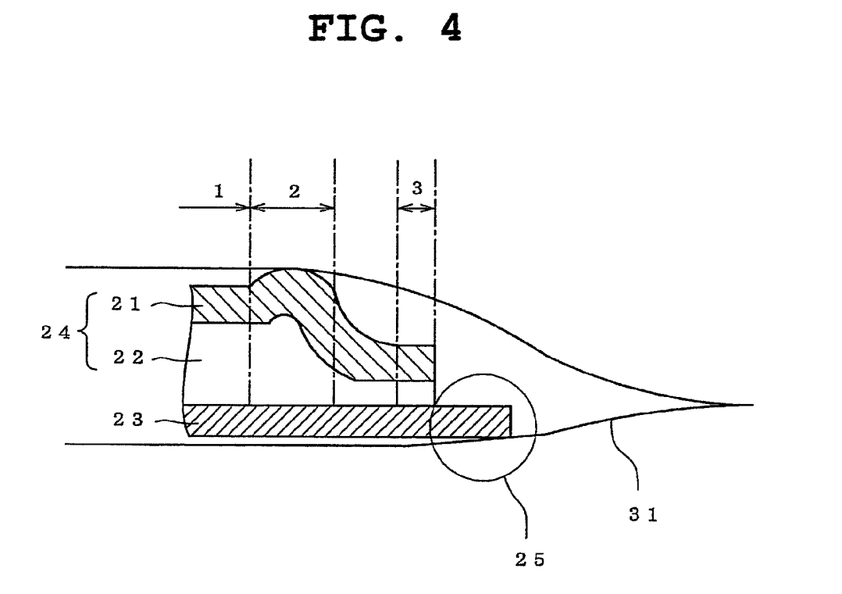
FIG. 4 is a schematic sectional view showing an extended part of the adhesive patch of the present invention contained in a package, wherein a release liner has the extended part.

As in the embodiment shown in FIG. 4, the release liner 23 of the adhesive patch of the present invention preferably has an extended part 25 outwardly extending over the adhesive patch main part 24. Since the extended part 25 decreases the frequency of contact of the edge of the adhesive patch main part 24 against the inside of the package 31 when the adhesive patch is contained in the package 31, even when an adhesive layer component is protruded or outflown from the edge of the adhesive patch main part 24, adhesion thereof to the inside of package 31 which causes difficulty in taking the adhesive patch out from the package 31 can be suppressed. The adhesive patch of the present invention may not have an extended part 25. To exert the aforementioned effect, however, at least a part of the peripheral part of the adhesive patch main part 24 preferably has a release liner 23 with an extended part 25, and more preferably, all peripheral part of the adhesive patch main part 24 has a release liner 23 with an extended part 25. While the extended length of the release liner is not limited, it is preferable that the release liner 23 extend from the adhesive patch main part 24 by 0.5-10 mm, more preferably about 1-3 mm. When the extended length is within this range, the aforementioned effect can be achieved and no problem occurs when it is contained in the package 31.

As for the production method of the adhesive patch and adhesive preparation as mentioned above, various methods are available. However, for industrial production, for example, the following method is preferable for high production efficiency.

A composition for adhesive layer formation is applied to one surface or both surfaces of a release liner and dried to give an adhesive layer. A support is laminated thereon to give an original sheet for adhesive patch punching. The composition for adhesive layer formation is preferably applied to one surface of the release liner to facilitate formation of a swelling of the intermediate part in the adhesive patch main part during heating and pressing an area corresponding to the peripheral part of the adhesive patch main part in an original sheet for adhesive patch punching which is placed on a table and the like as mentioned below. When an original sheet for adhesive patch punching is obtained by applying a composition for adhesive layer formation to both surfaces of a release liner, the adhesive patch of the present invention having an adhesive patch main part on both surfaces of a release liner can be obtained.

Alternatively, a composition for adhesive layer formation is applied to a support and dried to give an adhesive layer. A release liner is laminated thereon to give an original sheet for adhesive patch punching.

A method of the above-mentioned lamination is not particularly limited and, for example, a known method such as adhesion (e.g., adhesion including application of adhesive such as primer and the like, and the like), fusion bonding or melt-bonding (e.g., thermal fusion bonding, ultrasonic fusion bonding, high frequency-fusion bonding and the like), pressure bonding (including thermal pressure bonding), a combination of any of the above, and the like can be employed.

Figure 5:
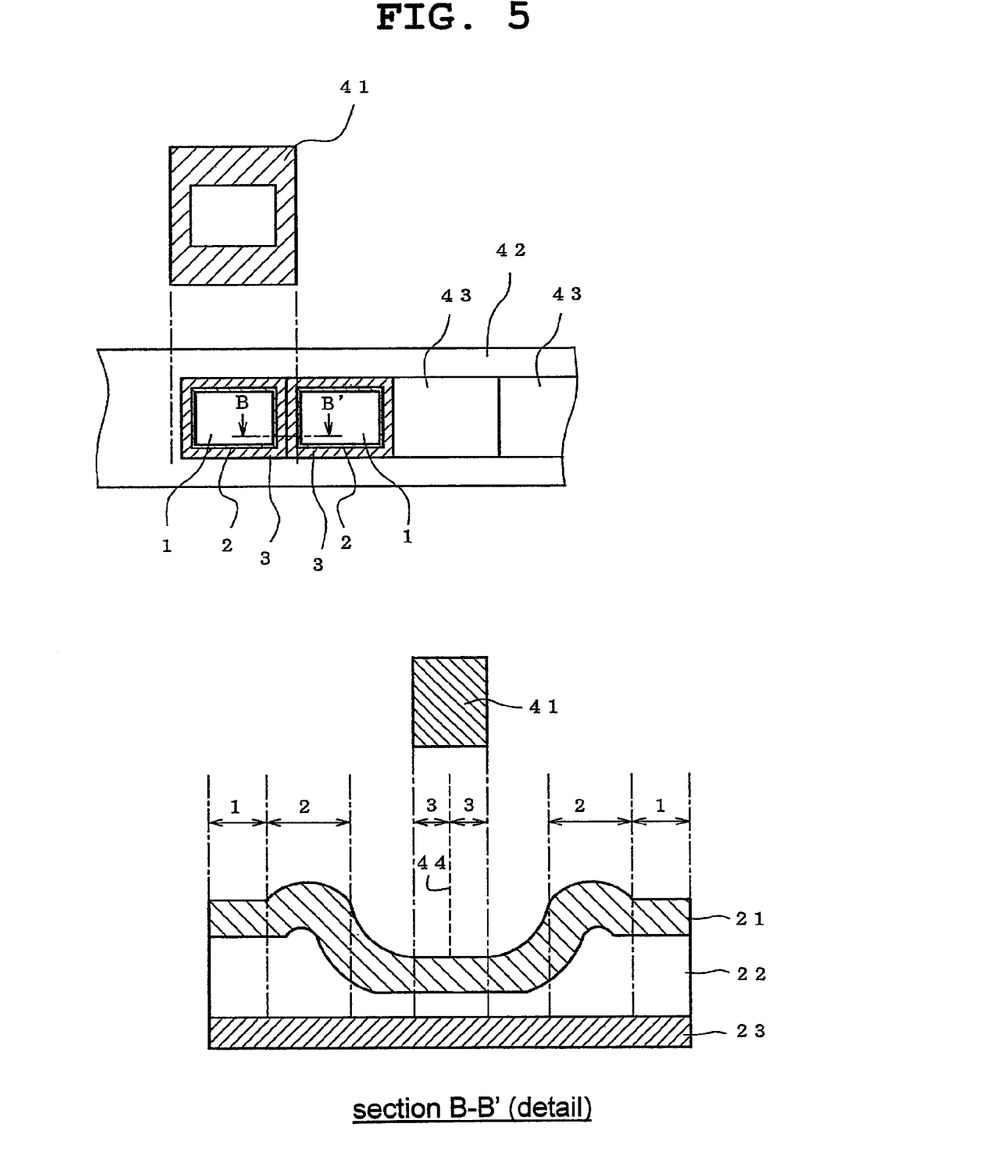
FIG. 5 schematically shows that areas corresponding to the peripheral part and the intermediate part can be formed by pressurization of the original sheet for adhesive patch punching with a heated stamp from the support side, and that the adhesive patch of the present invention can be efficiently produced from the original sheet by repeating the aforementioned pressurization and punching at a punching position where the adhesive patches make a line.

Then, as shown in FIG. 5, an original sheet for adhesive patch punching (hereinafter to be also simply referred to as an original sheet 42) is placed on a table and the like, and stamped from the support 21 side by pressing with a heated stamp 41 having a predetermined shape. After stamping, the original sheet is punched out at a first punching position such as 44 to give the adhesive patch of the present invention having a release liner. The aforementioned predetermined shape is such a shape as presses at least an area corresponding to the peripheral part 3 of the adhesive patch during pressing. By pressing an area corresponding to the peripheral part 3, a swollen portion corresponding to the intermediate part 2 can be formed. While the shape of the heated stamp 41 varies depending on the shape of the adhesive patch to be formed, for example, a flat plane shape defined by two rectangles on the same axis can be employed. For continuous production of adhesive patches, a second punching position 43 at which the adhesive patches form a line is assumed in an original sheet 42 and the stamping and punching are continuously repeated, whereby adhesive patches can be efficiently obtained from the original sheet 42.

Here, use of a heated stamp 41 is necessary. A heated stamp 41 softens a support comprising a resin film adjacent to the pressed area with heat, which in turn releases the adhesive layer in the pressed area, and encourages swelling of the area corresponding to the intermediate part 2. The adhesive patch main part corresponding to the once-swollen intermediate part 2 is later allowed to cool or cooled otherwise and maintains its shape.

The temperature of the heated stamp is preferably 90° C.-180° C., more preferably 120° C.-150° C.

The pressure to be applied is preferably 10-1000000 N/10 cm² ($1.0 \times 10^4$-$1.0 \times 10^9$ N/m²), more preferably 500-15000 N/10 cm² ($5.0 \times 10^5$-$1.5 \times 10^7$ N/m²). The pressing time is preferably 0.05-5 s, more preferably 0.1-1 s.

During stamping, the gap between the stamp and the table thereof is preferably (thickness of support+thickness of adhesive layer in the peripheral part+thickness of release liner)±10 μm.

While the material of the stamp is not particularly limited, iron is preferable. Stainless steel may develop heat distortion and the processing thereof may be difficult. Aluminum and brass can be processed easily, but duration of the stamp may be inferior.

The punching means is not particularly limited, and laser, press-cutting blade and the like can be employed. Since adjustment of cutting size and position adjustment are easy and a clear end surface can be obtained, an original sheet is preferably punched out with a press-cutting blade dies set (male type and female type).

In a preferable embodiment of the adhesive patch of the present invention, the release liner has an extended part in at least one part of the peripheral part of the adhesive patch main part and, in a more preferable embodiment, the release liner has an extended part in the whole peripheral part of the adhesive patch main part. An extended part of such at least one part of the peripheral part can be easily formed by punching out only the adhesive patch main part using a press-cutting blade dies set (male type and female type) having a required shape and then punching out the release liner.

The length of the extended release liner can be adjusted by changing the size difference in the press-cutting blade dies set male type and female type, and the length of the extended release liner can be extended by increasing the size difference.

The release liner can be easily peeled off. By peeling off the release liner, the adhesive patch of the present invention comprising an adhesive patch main part comprising a support and an adhesive layer laminated on the support can be obtained. The release liner can have a dividing line as necessary, which helps detach the release liner easily when in use of the adhesive patch.

EXAMPLES

The present invention is explained in more detail in the following by referring to Examples and Comparative Examples, which are not to be construed as limitative.

Examples 1-7

<Preparation of Composition for Adhesive Layer Formation>
(1) Preparation of Composition for Hard Adhesive Layer Formation High molecular weight polyisobutylene (viscosity average molecular weight $4 \times 10^6$), medium molecular weight polyisobutylene (viscosity average molecular weight $5 \times 10^4$), a tackifier (alicyclic saturated hydrocarbon resin, softening point 141° C. (ring and ball method)), and an organic liquid component (isopropyl myristate) were mixed at a weight ratio of 17:25:28:30 (total weight 7.5 kg) in the presence of a toluene/hexane mixed solution (weight ratio 1:1, 17.5 kg) to give a composition (total weight 25 kg) to be used for formation of a hard adhesive layer.
(2) Preparation of Composition for Soft Adhesive Layer Formation In the same manner as in the preparation of a composition for hard adhesive layer formation except that the aforementioned weight ratio was set to 14:28:28:30, a composition for soft adhesive layer formation was obtained.
<Preparation of Original Sheet>

A composition for hard adhesive layer formation or a composition for soft adhesive layer formation was applied to an easy-release surface of a release liner (thickness 75 μm) made from poly(ethylene terephthalate) (hereinafter to be also indicated as "PET") such that the thickness of the adhesive layer after drying was 160 μm, and dried in a drying machine (100° C.) to give a release liner comprising a hard adhesive layer or a soft adhesive layer (both non-cross-linked). The surface where the adhesive layer had been formed was adhered to a PET non-woven fabric surface of a support, which is a laminate (total thickness 40 μm) of a 4.5 μm-thick PET film and a 35 μm-thick PET non-woven fabric (basis weight 20 g/m²) by pressure bonding to give an original sheet for adhesive patch punching.
<Production of Adhesive Patch>

Using a heated stamp (outer size 64 mm×64 mm, inner size 56 mm×56 mm) having a flat plane defined by two almost square shapes on the same axis, the support surface of the original sheet for adhesive patch punching was heated and pressed (pressure 10000 N/10 cm² ($1 \times 10^7$ N/m²), time of heating and pressing 0.5 s). Heating was performed at various temperatures for respective Examples. An adhesive patch main part and a release liner were simultaneously punched out from the heated and pressed original sheet using a press-cutting blade dies set such that the heated and pressed area corresponded to the peripheral part of a adhesive patch to be obtained later, whereby the adhesive patch of the present invention free of an extended part was obtained. The obtained adhesive patch and the adhesive patch main part each had a square outline of about 60 mm one side, and had a band-like peripheral part (width about 1.5 mm) in the whole outer circumference, a square central part inside the peripheral part, and a band-like intermediate part between the central part and the peripheral part. The adhesive patch was tightly sealed in a packaging material (outer size 95 mm×95 mm, inner size 85 mm×85 mm) with an outer layer made of a 12 μm-thick PET film and an inner layer made of a 30 μm-thick polyacrylonitrile-based resin film to give an adhesive patch package having two V-shaped notches.

Example 8

In the same manner as in Examples 1-7 except that an extended part of a release liner was formed in the whole peripheral part of an adhesive patch main part by adjusting a size difference in the male type and female type of the press-cutting blade dies set, punching out an adhesive patch main part alone and then punching out the release liner, an adhesive patch was produced to give an adhesive patch package.

Comparative Example 1

An adhesive patch was produced in the same manner as in Examples 1-7 except that the stamping process was omitted and an adhesive patch package was produced.

Comparative Example 2

An adhesive patch was produced in the same manner as in Examples 1-7 except that the stamp was not heated and an adhesive patch package was produced.

Comparative Example 3

An adhesive patch was produced in the same manner as in Examples 1-7 except that a polyimide film was used as a resin film instead of the PET film and an adhesive patch package was produced.

Comparative Example 4

In the same manner as in Examples 1-7 except that an extended part of the release liner was formed in the whole peripheral part of an adhesive patch main part by adjusting a size difference in the male type and female type of the press-cutting blade dies set, punching out an adhesive patch main part alone and then punching out a release liner, and the stamping process was omitted, an adhesive patch was produced to give an adhesive patch package.

Experimental Example 1 (Evaluation of Adhesive Patch Shape)

The adhesive patch was stained with an aqueous ruthenium acid solution, and cut with a frozen microtome (LR-85 manufactured by YAMATO KOHKI INDUSTRIAL CO., LTD.). The section was taken by FE-SEM (Hitachi, S-4800) at 50- to 1000-power, and the gauge scales of the peripheral part, the intermediate part and the central part were read, whereby the thicknesses of the PET film and the PET non-woven fabric, and the thickness (total of thickness of adhesive layer and thickness of support) of the adhesive patch main part were measured. In this case, concaves and convexes are present on the surface of the PET non-woven fabric. In a sectional image, 10 convexes are selected at random, and an average of the thickness of the PET non-woven fabric at the convexes was calculated and taken as the thickness of the PET non-woven fabric. Then, the thickness of the PET film and the thickness of the aforementioned PET non-woven fabric were subtracted from the thickness of the adhesive patch main part, and the thicknesses of the adhesive layer at the peripheral part, the intermediate part and the central part were determined. As for the intermediate part, as shown by the adhesive layer at 2a, 2b and 2c in FIG. 1, the adhesive layer has different thickness for different position. Thus, the thickness of the adhesive layer for 2b in FIG. 1 was of the part having the maximum thickness. In Comparative Example 3, similarly, the thickness of the polyimide film was measured instead of the thickness of the PET film.

Experimental Example 2 (Evaluation of Take Out Performance of Adhesive Patch from Package)

Figure 6:
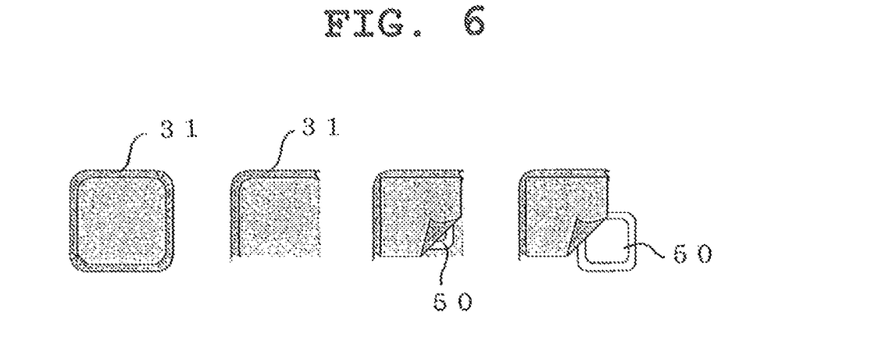
FIG. 6 shows that an adhesive patch package is opened by cutting two sides with scissors or along a V-shaped notch, and the adhesive patch is taken out.

As shown in FIG. 6, two sides of the adhesive patch package 31 were opened with scissors or along V-shaped notches. The adhesive patch 50 was taken out while holding a corner thereof, and the take out performance of the adhesive patch 50 from the package 31 was evaluated using 1-5 scores based on the following evaluation criteria.
<Evaluation Criteria>
5: can be taken out extremely easily with no protrusion of the adhesive layer
4: can be taken out extremely easily though the adhesive layer protrudes slightly
3: can be taken out easily though the adhesive layer protrudes somewhat
2: can be taken out though the adhesive layer protrudes somewhat
1: cannot be taken out easily since the adhesive layer protrudes considerably Experimental Example 3 (Evaluation of Skin Adhesion Performance)

A specialized estimator took out an adhesive patch from a package, adhered the patch to the chest for 24 hr from the morning, and evaluated the adhesion state using 1-5 scores based on the following evaluation criteria. During adhesion, the estimator behaved as usual. When the estimator took a bath in the morning, the patch was adhered immediately after taking a bath (within 30 min). The same estimator evaluated each Example and Comparative Example once.
<Evaluation Criteria>
5: adhesion of adhesive patch to the skin is maintained fine and the edge of adhesive patch does not turn up
4: adhesion of adhesive patch to the skin is maintained fine but the edge of adhesive patch slightly turns up
3: adhesion of adhesive patch to the skin is maintained fine but the edge of adhesive patch turns up in some parts
2: adhesion of adhesive patch to the skin is maintained but adhesiveness decreases as compared to initial stage of adhesion and the edge of adhesive patch turns up in some parts
1: adhesive patch falls off The evaluation results are shown in Table 1. In Table 1, "temperature" means the temperature of the surface subjected to pressing of a stamp. The "adhesive layer" is indicated as "(hard)" when a composition for hard adhesive layer formation was used and "(soft)" when a composition for soft adhesive layer formation was used. In Examples and Comparative Examples in which an extended part of a release liner was formed for the whole peripheral part, the average length is shown as "extended length".
Comparative Example 1 is an example without stamping,
Comparative Example 2 is an example without heating of stamp,
Comparative Example 3 is an example using polyimide film as a resin film instead of PET film, and Comparative Example 4 is an example with an extended part formed for a release liner and without stamping. In all Examples and Comparative Examples, the thickness of adhesive patch main part is a total of the thickness of adhesive layer and the thickness of support. Further, in Table 1 at *1) swelling of intermediate part disappeared in early stage after production.

TABLE 1

| | | | Evaluation results of adhesive patch | | | | | | |
|---|---|---|---|---|---|---|---|---|---|
| | temperature (° C.) | adhesive layer | thickness (μm) of adhesive layer | | | Width (mm) of peripheral part | extended length (mm) | take out performance | skin adhesion performance |
| | | | peripheral part | Intermediate part | central part | | | | |
| Comp. Ex. 1 | — | (hard) | 250 | 250 | 250 | 1.5 | 0 | | |
| Ex. 1 | 90 | (hard) | 200 | 265 | 250 | 1.5 | 0 | 3 | 2 |
| Ex. 2 | 120 | (hard) | 62 | 340 | 250 | 1.5 | 0 | 5 | 5 |
| Ex. 3 | 150 | (hard) | 50 | 330 | 250 | 1.5 | 0 | 4 | 5 |
| Comp. Ex. 2 | — | (hard) | 250 | 250 | 250 | 1.5 | 0 | 3 | 1 |
| Comp. Ex. 3 | 120 | (hard) | *1) | *1) | 250 | 1.5 | 0 | 3 | 1 |
| Ex. 4 | 90 | (hard) | 44 | 265 | 250 | 1.5 | 0 | 3 | 2 |
| Ex. 5 | 90 | (soft) | 35 | 290 | 250 | 1.5 | 0 | 2 | 2 |
| Ex. 6 | 120 | (soft) | 35 | 320 | 250 | 1.5 | 0 | 4 | 4 |

TABLE 1-continued

Evaluation results of adhesive patch

| | temperature (° C.) | adhesive layer | thickness (μm) of adhesive layer | | | Width (mm) of peripheral part | extended length (mm) | take out performance | skin adhesion performance |
|---|---|---|---|---|---|---|---|---|---|
| | | | peripheral part | Intermediate part | central part | | | | |
| Ex. 7 | 150 | (soft) | 28 | 325 | 250 | 1.5 | 0 | 3 | 4 |
| Ex. 8 | 120 | (hard) | 60 | 335 | 250 | 1.5 | 1.5 | 5 | 5 |
| Comp. EX. 4 | 120 | (hard) | 250 | 250 | 250 | 1.5 | 1.5 | 3 | 1 |

The adhesive patch of the present invention can be preferably used as a medical adhesive patch to cover and protect affected parts on the skin surface. When a drug is contained, it can be used as an adhesive preparation for continuous transdermal administration of a transdermally absorbable drug. In addition, the production method of the adhesive patch of the present invention can efficiently provide an adhesive patch and can be preferably used for industrial production.

The invention claimed is:

1. An adhesive patch comprising:
an adhesive patch main part including only a support and an adhesive layer laminated on the support, wherein
the support comprises a resin film comprising a thermoplastic resin, the resin film having a thickness of 1-45 μm,
the adhesive patch main part comprises a peripheral part, a central part, and an intermediate part between the peripheral part and the central part, the peripheral part being disposed peripherally relative to the central part in a horizontal direction,
the intermediate part of the adhesive patch main part has a thickness greater than that of the central part of the adhesive patch main part,
the central part of the adhesive patch main part has a thickness greater than that of the peripheral part of the adhesive patch main part,
the adhesive layer in the intermediate part has a thickness greater than that of the adhesive layer in the central part,
a thickness of the support is substantially constant from the peripheral part to the central part,
the support in the intermediate part of the adhesive patch main part has a curved convex portion,
a difference between a highest thickness of the adhesive patch main part in the intermediate part and the thickness of the adhesive patch main part in the peripheral part is 275-297 μm, a difference between the highest thickness of the adhesive patch main part in the intermediate part and the thickness of the adhesive patch main part in the central part is 70-90 μm, and a difference between the thickness of the adhesive patch main part in the central part and the thickness of the adhesive patch main part in the peripheral part is 188-222 μm,
the peripheral part is directly adjacent to the intermediate part, surrounds an outer periphery of the intermediate part, and has an outer edge that defines a complete outer periphery of the adhesive patch, and
the intermediate part has a region where the thickness of the adhesive layer is smaller than the thickness of the adhesive layer in the central part and a height of the support is higher than a height of the support in the central part.

2. The adhesive patch of claim 1, wherein the thermoplastic resin comprises poly(ethylene terephthalate).

3. The adhesive patch of claim 1, wherein the adhesive layer is not cross-linked.

4. The adhesive patch of claim 1, wherein the adhesive layer comprises an organic liquid component.

5. The adhesive patch of claim 1, wherein the adhesive layer comprises a drug.

6. The adhesive patch of claim 1, further comprising a release liner laminated on the adhesive layer, the release liner having an extended part outwardly extending beyond the adhesive patch main part.

7. The adhesive patch of claim 1, wherein, in the region of the intermediate part where the thickness of the adhesive layer is smaller than the thickness of the adhesive layer in the central part and the height of the support is higher than the height of the support in the central part, the thickness of the adhesive layer becomes increasingly smaller in a direction towards the peripheral part.

* * * * *